(12) United States Patent
Lin et al.

(10) Patent No.: US 11,954,250 B2
(45) Date of Patent: Apr. 9, 2024

(54) EYE TRACKING DEVICE AND EYE TRACKING METHOD

(71) Applicant: HTC Corporation, Taoyuan (TW)

(72) Inventors: Lun-Kang Lin, Taoyuan (TW); I-Han Tai, Taoyuan (TW)

(73) Assignee: HTC Corporation, Taoyuan (TW)

( * ) Notice: Subject to any disclaimer, the term of this patent is extended or adjusted under 35 U.S.C. 154(b) by 0 days.

(21) Appl. No.: 17/951,104

(22) Filed: Sep. 23, 2022

(65) Prior Publication Data

US 2023/0324987 A1    Oct. 12, 2023

Related U.S. Application Data

(60) Provisional application No. 63/328,749, filed on Apr. 8, 2022.

(51) Int. Cl.
*G06F 3/01*    (2006.01)
*A61B 3/113*    (2006.01)

(52) U.S. Cl.
CPC ............. *G06F 3/013* (2013.01); *A61B 3/113* (2013.01)

(58) Field of Classification Search
CPC .......... G06F 3/011; G06F 3/013; G06F 3/015; A61B 3/113
See application file for complete search history.

(56) References Cited

U.S. PATENT DOCUMENTS

| | | | | |
|---|---|---|---|---|
| 8,446,341 | B2* | 5/2013 | Amirparviz | A61B 5/6821 250/221 |
| 9,207,760 | B1* | 12/2015 | Wu | G06F 18/2113 |
| 10,580,349 | B2* | 3/2020 | Martin | G02B 17/0808 |
| 11,137,622 | B2* | 10/2021 | Mirjalili | G02C 7/049 |
| 11,662,814 | B2* | 5/2023 | Sun | G06T 7/70 345/29 |
| 2014/0081178 | A1* | 3/2014 | Pletcher | A61B 3/10 600/595 |
| 2021/0157133 | A1* | 5/2021 | De Bougrenet | G06F 3/011 |
| 2021/0311328 | A1* | 10/2021 | Mirjalili | G02C 7/049 |
| 2022/0317461 | A1* | 10/2022 | Maikim | G02B 27/0179 |

OTHER PUBLICATIONS

"Office Action of Taiwan Counterpart Application", issued on Dec. 4, 2023, p. 1-p. 7.

* cited by examiner

*Primary Examiner* — Mihir K Rayan
(74) *Attorney, Agent, or Firm* — JCIPRNET

(57) ABSTRACT

An eye tracking device and an eye tracking method are provided. The eye tracking device includes a sensor and multiple signal transmitting units. The sensor is disposed on an eyeball of a user. The sensor has multiple signal receiving units. The signal transmitting units are disposed around the sensor and surround the sensor. The signal transmitting units respectively transmit multiple transmitting signals. The signal receiving units receive the transmitting signals to respectively generate multiple sensing signals. The eye tracking device calculates a position of the eyeball according to the sensing signals.

17 Claims, 7 Drawing Sheets

EYE TRACKING DEVICE AND EYE TRACKING METHOD

CROSS-REFERENCE TO RELATED APPLICATION

This application claims the priority benefit of U.S. provisional application Ser. No. 63/328,749, filed on Apr. 8, 2022. The entirety of the above-mentioned patent application is hereby incorporated by reference herein and made a part of this specification.

TECHNICAL FIELD

The disclosure relates to an eye tracking device and an eye tracking method, and particularly to an eye tracking device and an eye tracking method that can be configured on an eyeball and execute an eye tracking action.

DESCRIPTION OF RELATED ART

Generally speaking, the electronic product applied to eye tracking technology captures an image of a human eye through a camera, and obtains a result of eye tracking according to the captured image through a device with a calculation function. However, the camera limits the configuration of the conventional electronic product, which affects the operating experience of a user.

SUMMARY

Embodiments of the disclosure provide an eye tracking device and an eye tracking method, which can eliminate the need for a camera and execute an eye tracking action.

The eye tracking device according to an embodiment of the disclosure includes a sensor and multiple signal transmitting units. The sensor is disposed on an eyeball of a user. The sensor has multiple signal receiving units. The signal transmitting units are disposed around the sensor and surround the sensor. The signal transmitting units respectively transmit multiple transmitting signals. The signal receiving units receive the transmitting signals to respectively generate multiple sensing signals. The eye tracking device calculates a position of the eyeball according to the sensing signals.

An embodiment of the disclosure further provides an eye tracking method. The eye tracking method includes the following steps. A sensor having multiple signal receiving units is disposed on an eyeball of a user. Multiple signal transmitting units are disposed around the sensor. The signal transmitting units surround the sensor. Multiple transmitting signals are respectively transmitted by the signal transmitting units. The transmitting signals are respectively received by the signal receiving units to generate multiple sensing signals. A position of the eyeball is calculated according to the sensing signals.

Based on the above, the eye tracking device and the eye tracking method according to the embodiments of the disclosure can receive the transmitting signals through the sensor disposed on the eyeball of the user to generate the sensing signals, so that the eye tracking device executes the eye tracking action according to the sensing signals. Therefore, eye tracking can be implemented without the configuration of a camera, and the application of eye tracking can be experienced anytime, anywhere.

In order for the features and advantages of the disclosure to be more comprehensible, the following specific embodiments are described in detail in conjunction with the drawings.

DETAILED DESCRIPTION OF DISCLOSED EMBODIMENTS

Figure 1:
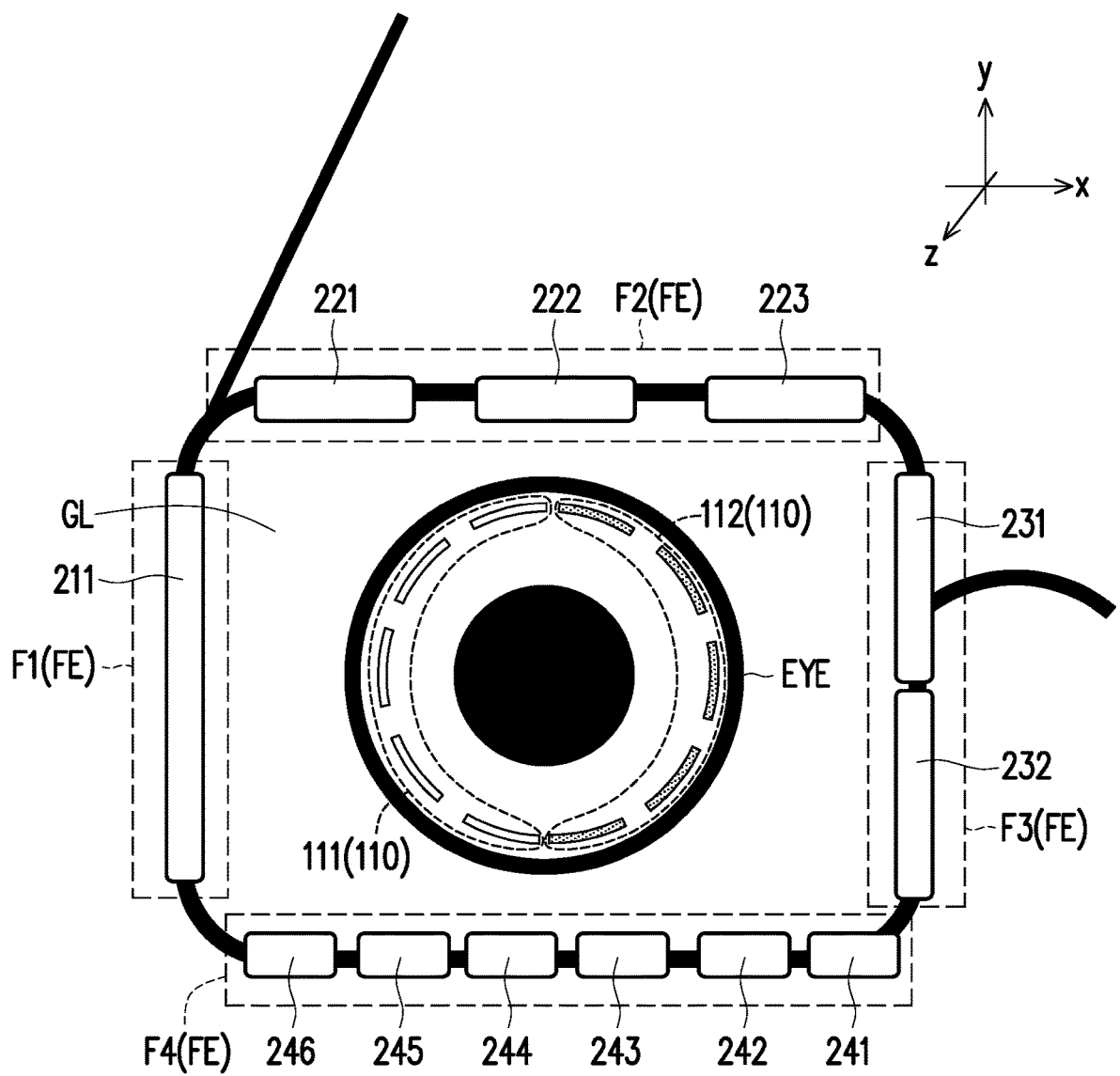
FIG. 1 is a schematic diagram of an eye tracking device according to an embodiment of the disclosure.

Some embodiments of the disclosure will be described in detail with reference to the drawings. Reference numerals referenced in the following description will be regarded as referring to the same or similar units when the same reference numerals appear in different drawings. The embodiments are only a part of the disclosure and do not disclose all possible implementations of the disclosure. Rather, the embodiments are only examples within the scope of the claims of the disclosure.

FIG. 1 is a schematic diagram of an eye tracking device according to an embodiment of the disclosure. Please refer to FIG. 1. An eye tracking device 100 may be coupled to an electronic device (not shown) to cooperate with the electronic device. For example, the eye tracking device 100 may be controlled by the electronic device to execute an operation. The electronic device may be, for example, a mobile phone, a tablet computer, a notebook computer, a desktop computer, etc.

In the embodiment of FIG. 1, the eye tracking device 100 includes a sensor 110 and multiple signal transmitting units 211 to 246. The sensor 110 is disposed on an eyeball EYE of a user. The signal transmitting units 211 to 246 are sequentially disposed around the sensor 110 and surround the sensor 110. In the embodiment, the signal transmitting units 211 to 246 may be distributed and asymmetrically disposed on a frame FE (for example, a frame of a head mounted display). The number and the configuration of the signal transmitting units 211 to 246 in the embodiment of FIG. 1 are only examples and are not limited thereto.

Based on the sensor 110 being disposed on the eyeball EYE of the user, the sensor 110 may change positions along with movements of the eyeball EYE.

In the embodiment, the sensor 110 has multiple signal receiving units 111 and 112. The signal receiving unit 111 and the signal receiving unit 112 may respectively include multiple segmented sensing coils (not shown). The sensing coils are sequentially disposed adjacent to an outer edge of the sensor 110 and surround a pupil (that is, a black solid circle in FIG. 1) of the eyeball EYE. The number and the configuration of the signal receiving units 111 and 112 in the embodiment of FIG. 1 are only examples and are not limited thereto.

In the embodiment, the sensor 110 may be, for example, a smart contact lens. The signal receiving unit 111 or 112 may be, for example, a planar printed antenna or other types of antennas for receiving wireless signals. In the embodiment, the signal transmitting units 211 to 246 may be, for example, planar printed antennas or other types of antennas for outputting wireless signals.

Figure 2:
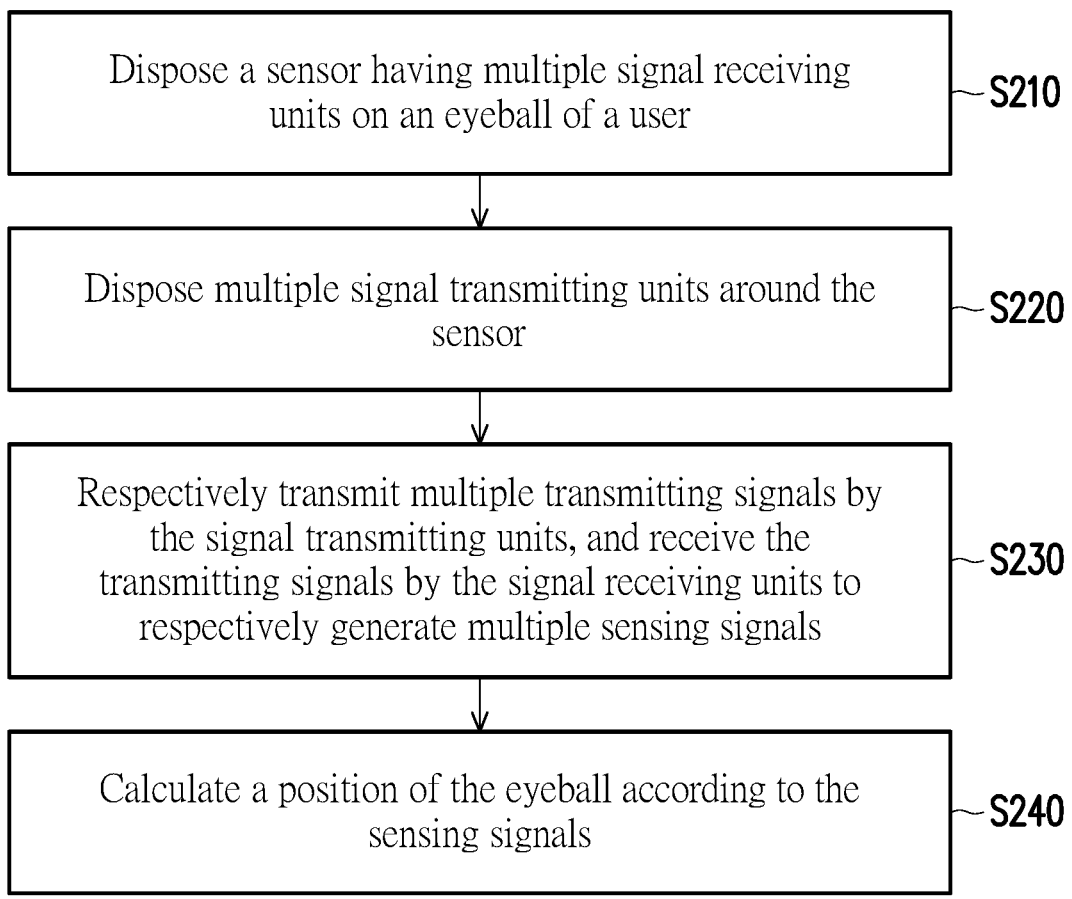
FIG. 2 is a flowchart of an eye tracking method according to an embodiment of the disclosure.

FIG. 2 is a flowchart of an eye tracking method according to an embodiment of the disclosure. Please refer to FIG. 1 and FIG. 2. The eye tracking device 100 may execute the eye tracking method according to Steps S210 to S240 below.

In Step S210, the sensor 110 having the signal receiving units 111 and 112 is disposed on the eyeball EYE of the user through the user wearing the sensor 110 on the eyeball EYE. In the embodiment, the sensor 110 may be worn on one eye. In some embodiments, the number of the sensors 110 may be two, which are respectively worn on both eyes.

In Step S220, the signal transmitting units 211 to 246 are disposed around the sensor 110 through the user wearing glasses having the frame FE.

In Step S230, the signal transmitting units 211 to 246 respectively transmit the transmitting signals through the eye tracking device 100, and the signal receiving units 111 and 112 receive the transmitting signals to respectively generate the sensing signals.

It should be noted that since the signal receiving unit 111 has multiple different distances relative to the signal transmitting units 211 to 246, the sensing signal generated by the signal receiving unit 111 has information related to the distances. The signal receiving unit 112 may be analogized by referring to the relevant description of the signal receiving unit 111, so there will be no repetition.

In Step S240, the eye tracking device 100 calculates a position of the eyeball EYE according to the sensing signals. In other words, the eye tracking device 100 can track the eyeball EYE according to distance information in the sensing signals. In the embodiment, the position of the eyeball EYE may be represented by rectangular coordinates (for example, (x, y, z)). In some embodiments, the position of the eyeball EYE may be represented by polar coordinates or other coordinate systems.

It is worth mentioning here that receiving the transmitting signals through the sensor 110 disposed on the eyeball EYE to generate the corresponding sensing signals can execute an eye tracking action according to the sensing signals, without the need for a camera to implement eye tracking, so as to further miniaturize the eye tracking device 100. On the other hand, the user can experience the application of eye tracking, such as an immersive experience combined with augmented reality (AR) or virtual reality (VR), anytime, anywhere through the eye tracking device 100.

Please refer to FIG. 1 again. In the embodiment, the eye tracking device 100 further includes a controller (not shown) and a power supply (not shown). The controller is coupled to the signal receiving units 111 and 112, the signal transmitting units 211 to 246, and the power supply. The controller may be disposed in the electronic device (not shown). The power supply may be disposed on the frame FE or in a glass GL sandwiched by the frame FE.

In the embodiment, the controller may turn on or off the signal receiving units 111 and 112 and/or the signal transmitting units 211 to 246. In the embodiment, the controller may control the power supply, so that the power supply charges the signal receiving units 111 and 112 and/or the signal transmitting units 211 to 246.

In the embodiment, the controller may be, for example, a field programmable gate array (FPGA), a central processing unit (CPU), other programmable general purpose or specific purpose microprocessors, digital signal processors (DSPs), programmable controllers, application specific integrated circuits (ASICs), programmable logic devices (PLDs), other similar devices, or a combination of the devices, which may load and execute relevant firmware or software to implement a calculation function.

In the embodiment of FIG. 1, the signal receiving units 111 and 112 may be distributed at different positions of the sensor 110. For example, the signal receiving unit 111 is disposed at an outer edge of a first side of the sensor 110, and the signal receiving unit 112 is disposed at an outer edge of a second side of the sensor 110, wherein the first side is opposite the second side. The signal receiving units 111 and 112 may be adjoined to form a closed loop. In some embodiments, the number of the signal receiving units 111 and 112 may be more than three and is not limited thereto.

In the embodiment, the signal transmitting units 211 to 246 are disposed on the frame FE (for example, the frame of the glasses). The frame FE may be a wraparound structure that is closed or has a gap to surround the sensor 110. For example, the frame FE includes a first holder F1, a second holder F2, a third holder F3, and a fourth holder F4. The first holder F1 to the fourth holder F4 are sequentially adjoined in a clockwise direction to form the wraparound structure. The shape of the frame FE and the number and the configuration of the holders F1 to F4 in the embodiment of FIG. 1 are only examples and are not limited thereto.

In the embodiment, the signal transmitting units 211 to 246 include at least one first signal transmitting unit 211, at least one second signal transmitting units 221 to 223, at least one third signal transmitting units 231 to 234, and at least one fourth signal transmitting units 241 to 246. The signal transmitting units 211 to 246 are sequentially distributed on the holders F1 to F4 of the frame FE in a clockwise direction.

In detail, in the embodiment, the first signal transmitting unit 211 may have a first number (for example, 1). The first signal transmitting unit 211 may extend in a Y direction and have a first size. The first signal transmitting unit 211 is disposed on the first holder F1 of the frame FE.

In the embodiment, the second signal transmitting units 221 to 223 may have a second number (for example, 3). The second signal transmitting unit 221 may extend in an X direction and have a second size. The second signal transmitting units 222 and 223 may be analogized by referring to the relevant description of the second signal transmitting unit 221, so there will be no repetition. The second signal transmitting units 221 to 223 may be distributed on the second holder F2.

In the embodiment, the third signal transmitting units 231 to 232 may have a third number (for example, 2). The third signal transmitting unit 231 may extend in the Y direction and have a third size. The third signal transmitting unit 231 is disposed on the third holder F3 of the frame FE. The third signal transmitting unit 232 may be analogized by referring to the relevant description of the third signal transmitting unit 231, so there will be no repetition. The third signal transmitting units 231 to 232 may be distributed on the third holder F3.

In the embodiment, the fourth signal transmitting units 241 to 246 may have a fourth number (for example, 6). The fourth signal transmitting unit 241 may extend in the X direction and have a fourth size. The fourth signal transmitting units 242 to 246 may be analogized by referring to the relevant description of the fourth signal transmitting unit 241, so there will be no repetition. The fourth signal transmitting units 241 to 246 may be distributed on the fourth holder F4.

It should be noted that the first size, the second size, the third size, and the fourth size are different in pairs. In other words, the structural sizes of the signal transmitting units disposed on different holders F1 to F4 are all different. The signal transmitting units are, for example, the first signal transmitting unit 211, the second signal transmitting unit 221, the third signal transmitting unit 231, and the fourth signal transmitting unit 241. On the other hand, the first number, the second number, the third number, and the fourth number are different in pairs. In other words, the number of signal transmitting units disposed on different holders F1 to F4 is different. The numbers are, for example, 1, 3, 2, and 6.

Figure 3:
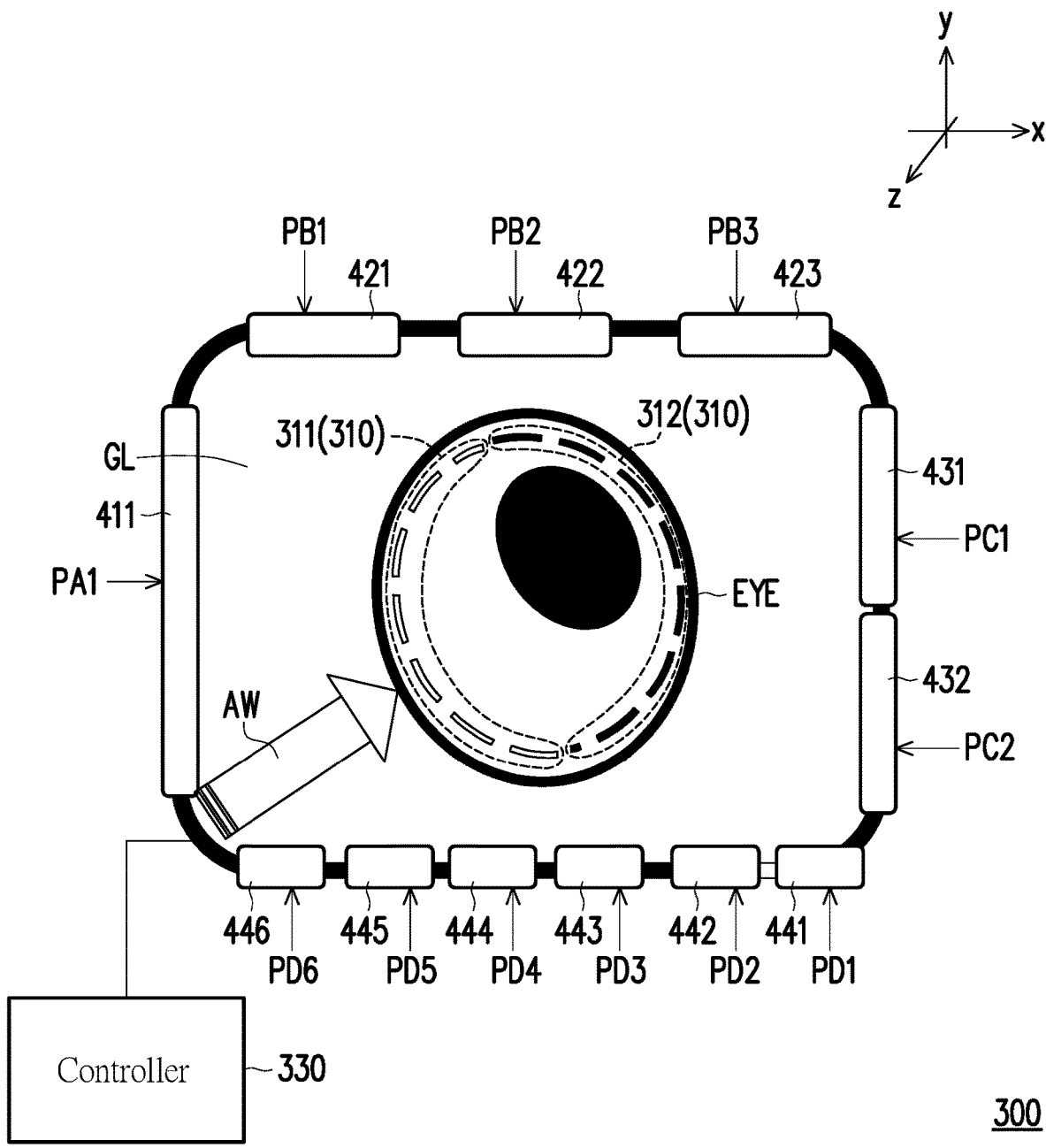
FIG. 3 is a schematic action diagram of an eye tracking device according to an embodiment of the disclosure.

FIG. 3 is a schematic action diagram of an eye tracking device according to an embodiment of the disclosure. Please refer to FIG. 3. A sensor 310, multiple signal transmitting units 411 to 446, a controller 330, and a power supply (not shown) included in an eye tracking device 300 may be analogized by referring to the relevant description of the eye tracking device 100, so there will be no repetition.

In the embodiment, when the eyeball EYE moves (for example, in the direction of an arrow AW), the sensor 310 moves along with the eyeball EYE. In other words, positions of multiple signal receiving units 311 and 312 respectively change relative to the signal transmitting units 411 to 446. At this time, the eye tracking device 300 may operate in a tracking mode to calculate the position of the eyeball EYE or may operate in a calibration mode to establish an eye movement model.

No matter in the tracking mode or the calibration mode, the power supply may output multiple charging signals PA1 to PD6 to the signal transmitting units 411 to 446. In detail, the first signal transmitting unit 411 may receive the charging signal PA1. The second signal transmitting units 421 to 423 may respectively receive the charging signals PB1 to PB3. The third signal transmitting units 431 to 432 may respectively receive the charging signals PC1 and PC2. The fourth signal transmitting units 441 to 446 may respectively receive the charging signals PD1 to PD6.

In the embodiment, the signal transmitting units 411 to 446 may respectively receive the charging signals PA1 to PD6 for charging. In some embodiments, the signal transmitting units 411 to 446 may respectively receive and transmit the charging signals PA1 to PD6 as transmitting signals to execute eye tracking. In some embodiments, the signal transmitting units 411 to 446 may respectively receive and transmit the charging signals PA1 to PD6 to charge the sensor 310.

Figure 4:
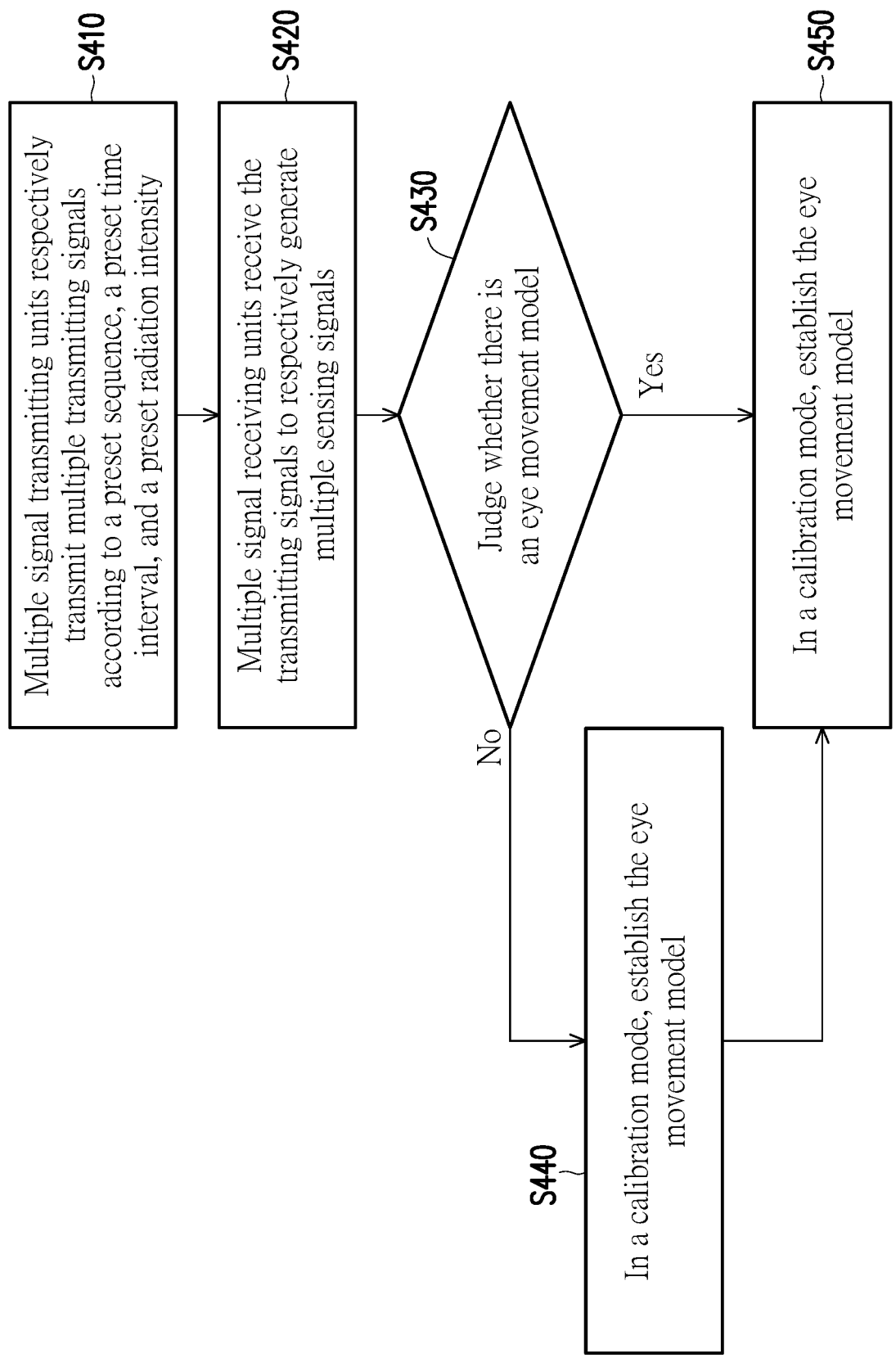
FIG. 4 is a flowchart of an eye tracking method shown in the embodiment of FIG. 3 according to the disclosure.

FIG. 4 is a flowchart of an eye tracking method shown in the embodiment of FIG. 3 according to the disclosure. Please refer to FIG. 3 and FIG. 4. The eye tracking device 300 may execute the eye tracking method according to Steps S410 to S450 below.

In Step S410, the signal transmitting units 411 to 446 respectively transmit the transmitting signals according to a preset sequence, a preset time interval, and a preset radiation intensity through the controller 330 controlling the signal transmitting units 411 to 446.

Figure 5A:
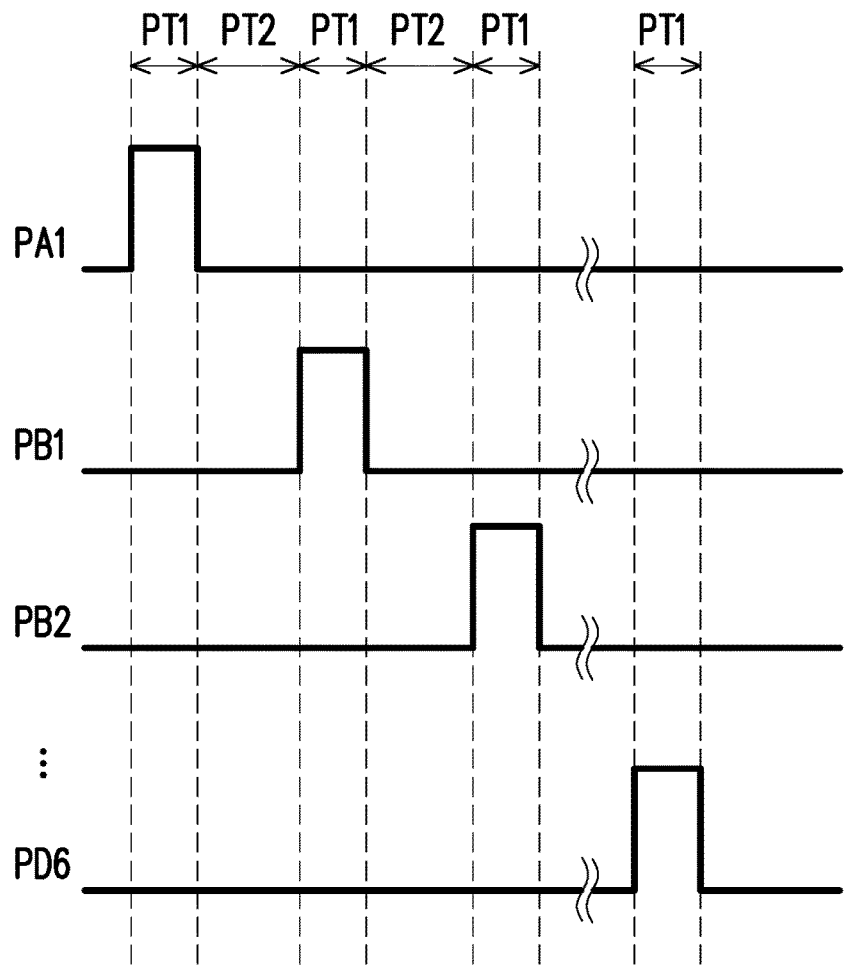
FIG. 5A is a schematic action diagram of a signal transmitting unit shown in the embodiment of FIG. 3 according to the disclosure.

For example, with an enabled sequence being clockwise, the signal transmitting units 411 to 446 sequentially transmit the transmitting signals with the same energy at the same time interval. Please refer to FIG. 5A together. FIG. 5A is a schematic action diagram of a signal transmitting unit shown in the embodiment of FIG. 3 according to the disclosure. In FIG. 5A, the horizontal axis is the operating time of the signal transmitting units 411 to 446, and the vertical axis is the voltage value. In the embodiment, the charging signals PA1 to PD6 are respectively used to charge the signal transmitting units 411 to 446 to transmit the corresponding transmitting signals. Each of the charging signals PA1 to PD6 has the same enabled period PT1 and has the same enabled voltage value. In addition, the time interval between the charging signals PA1 to PD6 is the same (that is, a period PT2).

In Step S420, the transmitting signals are received through the signal receiving units 311 and 312 to respectively generate multiple sensing signals.

Figure 5B:
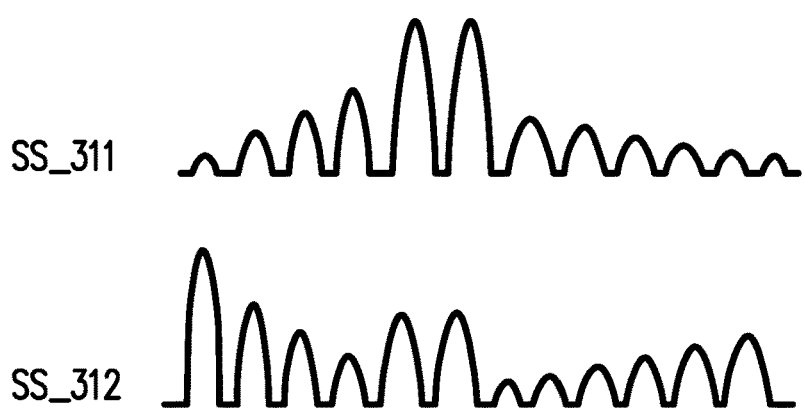
FIG. 5B is a schematic action diagram of a signal receiving unit shown in the embodiment of FIG. 3 according to the disclosure.

For example, please refer to FIG. 5B together. FIG. 5B is a schematic action diagram of a signal receiving unit shown in the embodiment of FIG. 3 according to the disclosure. In FIG. 5B, the horizontal axis is the operating time of the signal receiving units 311 and 312, and the vertical axis is the voltage value. In the embodiment, the signal receiving units 311 and 312 may receive (and accumulate) the transmitting signals within the period of Step S410 to respectively generate a first sensing signal SS_311 and a second sensing signal SS_312.

In Step S430, the controller 330 judges whether there is the eye movement model in the eye tracking device 300. If the result of Step S430 is no, it means that the eye movement model has not been established by the eye tracking device 300, and the eye tracking device 300 executes Step S440. If the result of Step S430 is yes, it means that the eye tracking device 300 has established the eye movement model, and the eye tracking device 300 executes Step S450.

In Step S440, the eye tracking device 300 operates in the calibration mode, and the eye movement model is established through the controller 330. In the embodiment, the eye tracking device 300 may continue to execute Step S450. Step S440 may include the following step details.

In the calibration mode, multiple different gazing directions of the eyeball EYE are sequentially set through the controller 330. The gazing directions may include directly gazing at the front (that is, the eyeball EYE is centered), a first direction (that is, a positive X direction), a second direction (that is, a negative X direction), a third direction (that is, a positive Y direction), a fourth direction (that is, a negative Y direction), etc. of own field of view. The number and the sequence of the gazing directions in the embodiment are only examples and are not limited thereto.

In the calibration mode, corresponding to each gazing direction, each signal transmitting unit 411 to 446 time-divisionally transmits each transmitting signal through the controller 330. In the embodiment, the transmitting signals may be, for example, the transmitting signals generated according to the charging signals PA1 to PD6 shown in FIG. 5A.

In the calibration mode, multiple classification boundary equations are established through the controller 330 according to waveforms of the sensing signals received by the signal receiving units 311 and 312. In the embodiment, the sensing signals may be, for example, the sensing signals SS_311 and SS_312 according to FIG. 5B.

Specifically, corresponding to each gazing direction, an energy average value of each sensing signal is calculated through the controller 330. In other words, when the eyeball EYE is gazing at the front (that is, the eyeball EYE is centered), the controller 330 calculates the energy average value of the sensing signal generated at that time. When the eyeball EYE is gazing in the positive X direction of an image, the controller 330 calculates the energy average value of the sensing signal generated at that time, and so on. In the embodiment, the controller 330 classifies the calculated energy average values according to classification decision analysis or other classification manners, so as to obtain the classification boundary equations associated with different gazing directions (for example, the center, the positive X direction, the negative X direction, the positive Y direction, and the negative Y direction) and the energy average values of the sensing signals.

In the calibration mode, classification calculation is performed through the controller 330 according to the gazing directions and the corresponding energy average values to establish the eye movement model. In other words, the eye movement model may include the classification boundary equations to classify the energy average values of the sensing signals into the corresponding gazing directions (for example, the center, the positive X direction, the negative X direction, the positive Y direction, and the negative Y direction).

On the other hand, in the calibration mode, in the embodiment, an eigenvalue and an eigenvector are calculated through the controller 330 according to an eigenequation (for example, Equation $A \times B = C \times B$). In the equation, A is a vector formed by the energy average values corresponding to each gazing direction in the calibration mode, B is the eigenvector to represent a relationship between the gazing direction and the energy average value of the sensing signal, and C is the eigenvalue in the relationship, wherein the dimension of A may be 5×5, the dimension of B may be 5×1, and C may be a constant.

In the calibration mode, the controller 330 establishes the eye movement model through storing the eigenvalue (that is, the eigenvalue C) and the eigenvector (that is, the eigenvector B). In other words, in each classification boundary equation (corresponding to a single gazing direction), the eye movement model may include the eigenvalue C and the eigenvector B to calculate the energy average value of the sensing signal and the eigenvector B and/or the eigenvalue C, so as to obtain the position of the eyeball EYE.

In some embodiments, in Step S440, the eye tracking device 300 operates in the calibration mode, and a gazing vector lookup table is established through the controller 330. In the calibration mode, outer product of the energy average value of each sensing signal and the eigenvector are found through the controller 330 according to the classification boundary equation to generate a search distance. A distance vector corresponding to each gazing direction is drawn through the controller 330 using an interpolation method (for example, an interpolation method), and multiple distance vectors are stored in the gazing vector lookup table.

In Step S450, the eye tracking device 300 operates in the tracking mode, and each sensing signal is calculated through the controller 330 to calculate the position of the eyeball EYE. In other words, the eye tracking device 300 may bring the sensing signal into the eye movement model for calculation, so as to obtain the position of the eyeball EYE.

In other embodiments of the disclosure, the calibration mode may also be performed by means of machine learning through the controller 330. For example, the controller 330 may set a neural network model, and input the obtained energy average values of the sensing signals associated with different gazing directions into the neural network model for training. In addition, in the tracking mode, the controller 330 may input each sensing signal into the trained neural network model, thereby calculating the position of the eyeball EYE.

Figure 6:
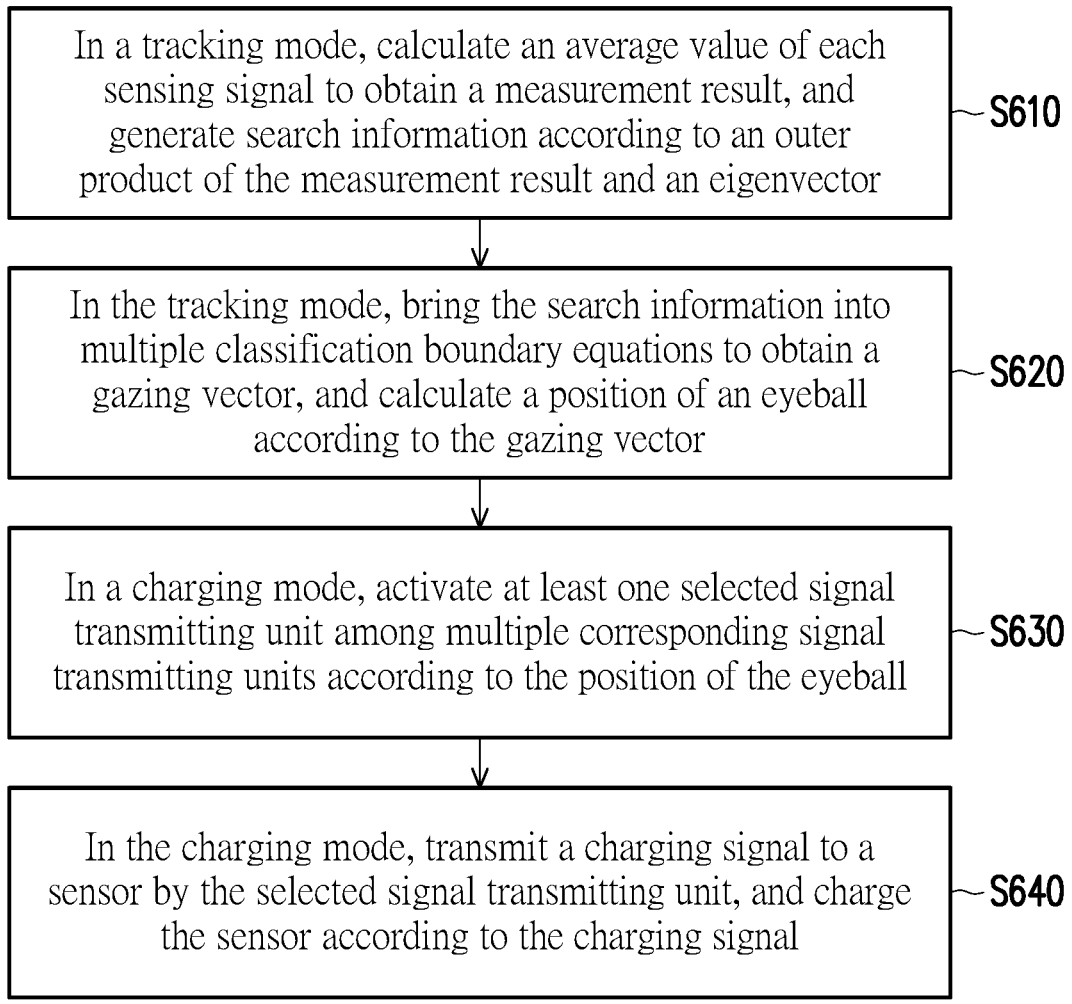
FIG. 6 is a flowchart of an eye tracking method shown in the embodiment of FIG. 3 according to the disclosure.

FIG. 6 is a flowchart of an eye tracking method shown in the embodiment of FIG. 3 according to the disclosure. Please refer to FIG. 3 and FIG. 6. The eye tracking device 300 may execute the eye tracking method according to Steps S610 to S640 below.

In Step S610, the eye tracking device 300 operates in the tracking mode, an average value (for example, an energy average value) of each sensing signal is calculated through the controller 330 to obtain a measurement result, and outer product of the measurement result and the eigenvector (that is, the eigenvector B in the eye movement model) are found to generate search information. In other words, the controller 330 may calculate the energy average values of the sensing signals (that is, the measurement results represented by vectors). The controller 330 may bring the measurement result into an eigenequation to obtain the search information represented by vectors.

In Step S620, the eye tracking device 300 operates in the tracking mode, the search information is brought into multiple classification boundary equations (that is, the classification boundary equations in the eye movement model) through the controller 330 to obtain a gazing vector, and the position of the eyeball EYE is calculated according to the gazing vector.

In Step S630, the eye tracking device 300 operates in a charging mode in the tracking mode, and at least the selected signal transmitting units (for example, the signal transmitting units 422 and 423) among the corresponding signal transmitting units 411 to 446 are activated through the controller 330 according to the position of the eyeball EYE (for example, as shown in FIG. 3).

In Step S640, the eye tracking device 300 operates in the charging mode, a power supply is controlled through the controller 330, so that the selected signal transmitting units (for example, the signal transmitting units 422 and 423) transmit charging signals (for example, charging signals PB2 and PB3) to the sensor 310, so that the sensor 310 is charged according to the charging signals.

Figure 7:
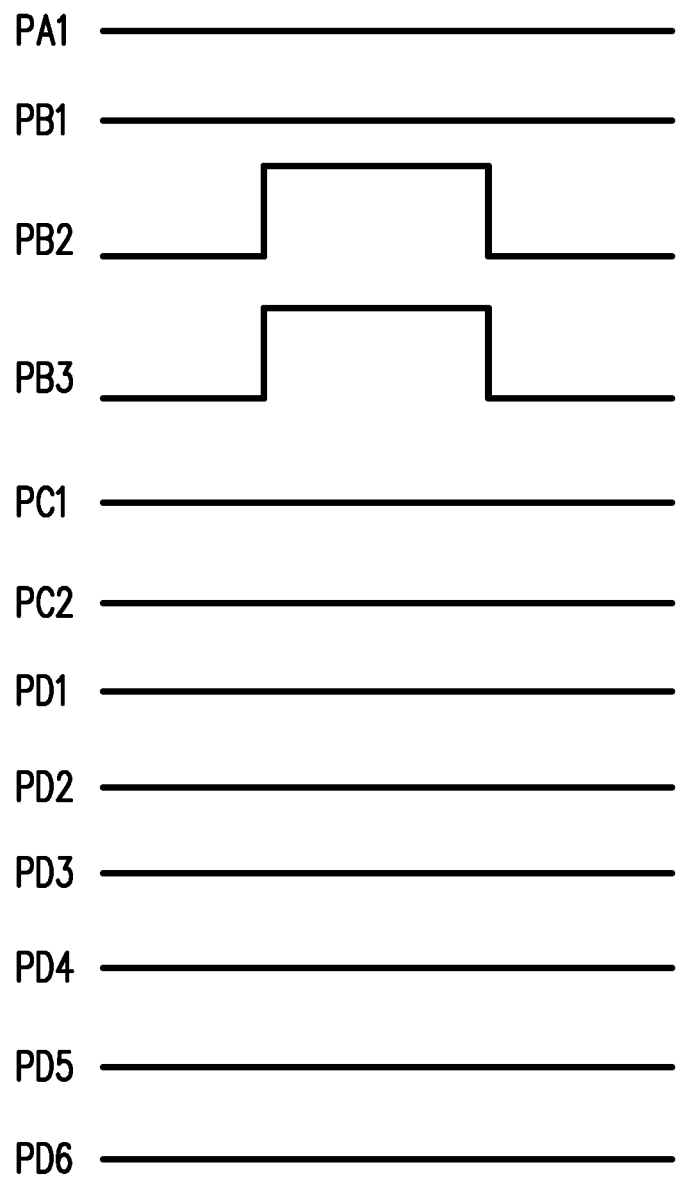
FIG. 7 is a schematic action diagram of a signal receiving unit shown in the embodiment of FIG. 6 according to the disclosure.

For example, please refer to FIG. 7 together. FIG. 7 is a schematic action diagram of a signal receiving unit shown in the embodiment of FIG. 6 according to the disclosure. In FIG. 7, the horizontal axis is the operating time of the signal receiving units 311 and 312, and the vertical axis is the voltage value. In the embodiment, when the controller 330 has calculated the position of the eyeball EYE (for example, as shown in FIG. 3), the controller 330 may choose to drive the signal transmitting units 422 and 423. The chosen signal transmitting units 422 and 423 respectively receive the charging signals PB2 and PB3 having enabled voltages for charging. The other unchosen signal transmitting units 411, 421, and 431 to 446 do not receive the charging signals (that is, the charging signals PA1, PB1, and PC1 to PD6 that do not have enabled voltages). The chosen signal transmitting units 422 and 423 respectively transmit the charging signals PB2 and PB3, so that the sensor 310 receives the charging signals PB2 and PB3 for charging.

It should be noted that, the signal transmitting units 422 and 423 adjacent to the position of the eyeball EYE may be chosen through the eye tracking device 300 according to the position of the eyeball EYE and/or the configurations (size, number, etc.) of the signal transmitting units 411 to 426. In this way, the eye tracking device 300 can achieve the minimum output power to improve the operating stability of the eye tracking device 300 through enabling the signal transmitting units 422 and 423, so as to further reduce the radiation energy that a human body may absorb.

In summary, the eye tracking device and the eye tracking method according to the embodiments of the disclosure can execute the eye tracking action through the sensor disposed on the eyeball, so as to improve the experience of the user. In some embodiments, according to the calculated position of the eyeball, the eye tracking device can enable a part of the signal transmitting units to charge the sensor, so as to reduce the power consumption of the eye tracking device and achieve the minimum output power.

Although the disclosure has been disclosed in the above embodiments, the embodiments are not intended to limit the disclosure. Persons skilled in the art may make some changes and modifications without departing from the spirit and scope of the disclosure. Therefore, the protection scope of the disclosure shall be defined by the appended claims.

What is claimed is:

1. An eye tracking device, comprising:
a sensor, disposed on an eyeball of a user and having a plurality of signal receiving units; and
a plurality of signal transmitting units, disposed around the sensor and surrounding the sensor,
wherein the signal transmitting units respectively transmit a plurality of transmitting signals in a preset sequence, the signal receiving units receive the transmitting signals to respectively generate a plurality of sensing signals, and the eye tracking device calculates a position of the eyeball according to the sensing signals,
wherein at least one of the signal transmitting units are selected to transmit a charging signal to the sensor for charging the sensor according to the position of the eyeball.

2. The eye tracking device according to claim 1, wherein the sensor moves along with the eyeball.

3. The eye tracking device according to claim 1, further comprising:
a controller, coupled to the signal receiving units.

4. The eye tracking device according to claim 3, wherein in a calibration mode, a plurality of different gazing directions of the eyeball are sequentially set, and corresponding to each of the gazing directions, each of the signal transmitting units time-divisionally transmits each of the transmitting signals,
the controller is used to:
establish a plurality of classification boundary equations according to waveforms of the sensing signals;
corresponding to each of the gazing directions, calculate an average energy value of each of the sensing signals; and
perform classification calculation according to the gazing directions and the corresponding energy average values to establish an eye movement model.

5. The eye tracking device according to claim 4, wherein the controller is further used to:
calculate an eigenvalue and an eigenvector according to an equation $A \times B = C \times B$, where A is the average energy values corresponding to the gazing directions, B is the eigenvector, and C is the eigenvalue; and
store the eigenvalue and the eigenvector to establish the eye movement model.

6. The eye tracking device according to claim 5, wherein in a tracking mode, the controller is used to:
calculate an average value of each of the sensing signals to obtain a measurement result, and generate search information according to an outer product of the measurement result and the eigenvector;
bring the search information into the classification boundary equations to obtain a gazing vector, and calculate the position of the eyeball according to the gazing vector.

7. The eye tracking device according to claim 1, wherein in a charging mode, the controller is used to:
activate the at least one selected signal transmitting unit among the corresponding signal transmitting units according to the position of the eyeball; and
transmit the charging signal to the sensor by the selected signal transmitting unit, and charge the sensor according to the charging signal.

8. The eye tracking device according to claim 1, wherein the signal transmitting units are disposed on a frame, the frame surrounds the sensor, and the signal receiving units are distributed at different positions of the sensor.

9. The eye tracking device according to claim 8, wherein the signal transmitting units comprise at least one first signal transmitting unit, at least one second signal transmitting unit, at least one third signal transmitting unit, and at least one fourth signal transmitting unit,
wherein the at least one first signal transmitting unit is disposed on a first holder of the frame; the at least one second signal transmitting unit is disposed on a second holder of the frame; the at least one third signal transmitting unit is disposed on a third holder of the frame; and the at least one fourth signal transmitting unit is disposed on a fourth holder of the frame.

10. The eye tracking device according to claim 9, wherein the at least one first signal transmitting unit, the at least one second signal transmitting unit, the at least one third signal transmitting unit, and the at least one fourth signal transmitting unit respectively have a first size, a second size, a third size, and a fourth size, and the first size, the second size, the third size, and the fourth size are different in pairs.

11. The eye tracking device according to claim 9, wherein the at least one first signal transmitting unit, the at least one second signal transmitting unit, the at least one third signal transmitting unit, and the at least one fourth signal transmitting unit respectively have a first number, a second number, a third number, and a fourth number, and the first number, the second number, the third number, and the fourth number are different in pairs.

12. An eye tracking method, comprising:
disposing a sensor having a plurality of signal receiving units on an eyeball of a user;
disposing a plurality of signal transmitting units around the sensor, wherein the signal transmitting units surround the sensor;
respectively transmitting a plurality of transmitting signals in a preset sequence by the signal transmitting units, and receiving the transmitting signals by the signal receiving units to respectively generate a plurality of sensing signals;
calculating a position of the eyeball according to the sensing signals; and
selecting at least at least one of the signal transmitting units to transmit a charging signal to the sensor for charging the sensor according to the position of the eyeball.

13. The eye tracking method according to claim 12, wherein the sensor moves along with the eyeball.

14. The eye tracking method according to claim 12, wherein in a calibration mode, the eye tracking method further comprises:
sequentially setting a plurality of different gazing directions of the eyeball;

corresponding to each of the gazing directions, time-divisionally transmitting each of the transmitting signals by each of the signal transmitting units;

establishing a plurality of classification boundary equations according to waveforms of the sensing signals;

corresponding to each of the gazing directions, calculating an average energy value of each of the sensing signals; and performing classification calculation according to the gazing directions and the corresponding energy average values to establish an eye movement model.

15. The eye tracking method according to claim 14, further comprising:

calculating an eigenvalue and an eigenvector according to an equation A×B=C×B, where A is the average energy values corresponding to the gazing directions, B is the eigenvector, and C is the eigenvalue; and storing the eigenvalue and the eigenvector to establish the eye movement model.

16. The eye tracking method according to claim 15, wherein in a tracking mode, the eye tracking method further comprises:

calculating an average value of each of the sensing signals to obtain a measurement result, and generating search information according to an outer product of the measurement result and the eigenvector;

bringing the search information into the classification boundary equations to obtain a gazing vector, and calculating the position of the eyeball according to the gazing vector.

17. The eye tracking method according to claim 12, wherein in a charging mode, the eye tracking method further comprises:

activating the at least one selected signal transmitting unit among the corresponding signal transmitting units according to the position of the eyeball; and transmitting the charging signal to the sensor by the selected signal transmitting unit, and charging the sensor according to the charging signal.

* * * * *